United States Patent [19]
O'Donnell et al.

[11] Patent Number: 5,615,675
[45] Date of Patent: Apr. 1, 1997

[54] METHOD AND SYSTEM FOR 3-D ACOUSTIC MICROSCOPY USING SHORT PULSE EXCITATION AND 3-D ACOUSTIC MICROSCOPE FOR USE THEREIN

[75] Inventors: Matthew O'Donnell; James D. Hamilton, both of Ann Arbor, Mich.

[73] Assignee: Regents of the University of Michigan, Ann Arbor, Mich.

[21] Appl. No.: 635,361

[22] Filed: Apr. 19, 1996

[51] Int. Cl.$^6$ ...................................................... A61B 8/00
[52] U.S. Cl. .................................... 128/653.1; 128/660.02
[58] Field of Search ............................ 128/653.1, 660.02; 73/627, 656; 374/45, 17, 57; 356/432, 436

[56] References Cited

U.S. PATENT DOCUMENTS

| | | |
|---|---|---|
| 4,006,444 | 2/1977 | Quate et al. . |
| 4,028,933 | 6/1977 | Lemons et al. . |
| 4,267,732 | 5/1981 | Quate . |
| 4,430,897 | 2/1984 | Quate . |
| 4,468,136 | 8/1984 | Murphy et al. ........................... 374/45 |
| 4,512,197 | 4/1985 | von Gutfeld et al. . |
| 4,710,030 | 12/1987 | Tauc et al. . |
| 5,269,309 | 12/1993 | Fort et al. . |
| 5,319,977 | 6/1994 | Quate et al. . |
| 5,465,722 | 11/1995 | Fort et al. . |
| 5,483,961 | 1/1996 | Kelly et al. ........................... 128/653.1 |

OTHER PUBLICATIONS

"Optical Detection of Ultrasound", Jean–Pierre Monchalin, IEEE Transactions on Ultrasonics, Ferroelectrics and Frequency Control, No. 5, Sep. 1986, pp. 485–498.

"Generation of Elastic Waves by Transient Surface Heating", R. M. White, Journal of Applied Physics, vol. 34, No. 12, Dec. 1963, pp. 3559–3567.

"Thermoelastic Generation of Elastic Waves for Non-Destructive Testing and Medical Diagnosis", R. J. Von Gutfeld, Ultrasonics, Jul. 1980, pp. 175–181.

"Ultrasonic Noncontact Inspection System with Optical Fiber Methods", A.J.A. Bruinsma J.A. Vogel, Applied Optics, vol. 27, No. 22, Nov. 15, 1988, pp. 4690–4695.

*Primary Examiner*—George Manuel
*Attorney, Agent, or Firm*—Brooks & Kushman P.C.

[57] ABSTRACT

A method and system are provided for 3-D acoustic microscopy using short pulse laser excitation. A 3-D acoustic microscope for use in such a system is also provided. In a first embodiment, wherein optical detection is utilized, a focused excitation beam is scanned by a first acoustooptic scanning device across an absorbing layer of an optoacoustic transducer (if needed) coupled to an object under investigation to create spherical ultrasonic waves within the object which may be living tissue. The reflected spherical ultrasonic waves are detected through the use of an unfocused probe beam and an optical detector array or a focused probe beam and a single photodetector which receive the probe beam from a reflecting surface of the opto-acoustic transducer. A second acoustooptic scanning device scans the probe beam at a plurality of positions on the reflecting surface of the opto-acoustic transducer. In another embodiment, an ultrasound transducer is utilized to acoustically detect the reflected spherical ultrasonic waves. Signals from the optical detector array, the photodetector, or the ultrasound transducer are subsequently digitized and reconstructed via 3-D synthetic aperture beam-forming equations to generate a 3-D representation of the object. Then the 3-D representation of the image is displayed as an image. The microscope includes the first and second acoustooptic scanning devices and the opto-acoustic transducer housed in a housing to define a needle probe such as a conventional biopsy needle.

58 Claims, 5 Drawing Sheets

METHOD AND SYSTEM FOR 3-D ACOUSTIC MICROSCOPY USING SHORT PULSE EXCITATION AND 3-D ACOUSTIC MICROSCOPE FOR USE THEREIN

CROSS-REFERENCE TO RELATED APPLICATION

This application is related to U.S. patent application entitled "Active Fiber-Optic Opto-Acoustic Detector," having the same assignee and filed on the same day as the present application. This application is hereby incorporated by reference in its entirety herein.

TECHNICAL FIELD

This invention relates to the non-destructive evaluation of objects and materials and, in particular, to method and systems for 3-D acoustic microscopy using short pulse excitation and 3-D acoustic microscopes for use therein.

BACKGROUND ART

The practice of clinical pathology centers around the microscopic analysis of biopsies obtained from the body. Although tissue biopsies are fundamentally three-dimensional, they must be sectioned for two-dimensional analysis by light microscopy because of the opaqueness of most biological specimens. As a consequence, multiple two-dimensional samples must be prepared for each biopsy. Sample preparation can be very costly for each section. Moreover, to accurately characterize the properties of the entire 3-D sample, a large number of sections must be prepared.

Acoustic microscopy is a well established technique dating to the early 1970s. The most recognized system was produced in the Applied Physics Department at Stanford University by Calvin Quate. U.S. Pat. Nos. 4,006,444; 4,028,933; 4,267,732; 4,430,897; and 5,319,977 disclose various acoustic microscopes wherein Mr. Quate is a named inventor.

Several small commercial versions of this microscope, and similar microscopes, have been produced over the last decade. All of these microscopes are inherently two-dimensional, where an image is commonly obtained through some form of mechanical scanning.

Short pulse laser excitation of acoustic waves is also a well established technique for ultrasonic frequencies less than 100 MHz. A large body of work was done on this at IBM by von Gutfeld in the early 1980s as described in the U.S. Pat. No. 4,512,197 to von Gutfeld et al.

Recent work by a group in the Physics Department at Brown University led by Tauc and Maris has shown that laser excitation can be extended to produce ultrasonic pulses at frequencies greater than 1 GHz. U.S. Pat. No. 4,710,030 in the name of Tauc et al. discloses some of this work.

Synthetic Aperture techniques are common in ultrasonic and RADAR systems as disclosed in the U.S. Pat. Nos. 5,269,309 and 5,465,722 to Fort et al. For example, Synthetic Aperture Radar (SAR), pioneered by ERIM over two decades ago, is now routinely used in many forms of surveillance.

However, all work to date on laser-generated, high frequency, acoustic waves uses weakly focused optical sources, resulting in spatially extended excitation (i.e., equivalent aperture many ultrasonic wavelengths across). Such excitation produces nearly plane wave propagation of the resultant ultrasonic pulse.

SUMMARY OF THE INVENTION

An object of the present invention is to provide a method and system for examining an object internally using the principles of acoustic microscopy, optical excitation of acoustic pulses and synthetic aperture reconstruction for the production of true 3-D acoustic microscope images. These techniques can be applied to human pathology and ultrasonic non-destructive testing.

Another object of the present invention is to provide a method and system for 3-D acoustic microscopy using short pulse excitation wherein living tissue can be investigated three dimensionally with the same diagnostic accuracy as current 2-D methods.

It is still another object of the present invention to provide a 3-D acoustic microscope which can be integrated into an optical needle probe such as the tip of a conventional biopsy needle so that in situ imaging of internal organs can be performed in real-time. Such an instrument will not remove any tissue from the organ under investigation.

Yet still another object of the present invention is to provide a method and system for 3-D acoustic microscopy using short pulse excitation for 3-D imaging of optically opaque small tissue samples with high frequency ultrasound.

It is still another object of the present invention to provide a method and system for 3-D acoustic microscopy using short pulse laser excitation and synthetic aperture reconstruction to produce dynamically focused 3-D images of small tissue samples with a resolution approaching the finest of optical microscopes.

Yet still a further object of the present invention is to provide a method and system for 3-D acoustic microscopy using short pulse excitation in a simple and effective manner for obtaining true 3-D acoustic microscopic images with near optimal resolution over a wide depth of field.

In carrying out the above objects and other objects of the present invention, a method is provided for examining an object internally. The method includes the steps of positioning an opto-acoustic transducer having an optically reflecting surface and an absorbing layer capable of converting a burst of electromagnetic energy into a thermal pulse relative to the object so that the thermal pulse propagates as an acoustic wave in the object and is internally reflected within the object. The method also includes the steps of scanning a plurality of bursts of the electromagnetic energy over the surface of the absorbing layer to obtain acoustic waves in the object, detecting acoustic waves reflected within the object at a plurality of positions at the optically reflecting surface of the opto-acoustic transducer to generate resultant signals, and calculating a 3-D representation of the object from the resultant signals. Finally, the method includes the step of displaying the 3-D representation as an image.

Still further in carrying out the above objects and other objects of the present invention, a method is provided for examining an object internally. The object is capable of converting a burst of electromagnetic energy into a thermal pulse which propagates as an acoustic wave in the object and is internally reflected within the object. The method includes the steps of scanning a plurality of bursts of the electromagnetic energy over a surface of the object to generate acoustic waves in the object, detecting the acoustic waves reflected within the object at a plurality of positions on the surface of the object to generate resultant signals, and calculating a 3-D representation of the object from the resultant signals. Finally, the method includes the step of displaying the 3-D representation as an image.

In carrying out the above objects and other objects of the present invention, systems are provided for carrying out the above method steps.

Yet still further in carrying out the above objects and other objects of the present invention, a 3-D acoustic microscope is provided and is adapted to be used in a system for 3-D acoustic microscopy to examine an object internally. The microscope includes an opto-acoustic transducer adapted to be coupled to the object. The transducer has an optically reflecting surface and an absorbing layer capable of converting a burst of electromagnetic energy into a thermal pulse which propagates as an acoustic wave in the object and is internally reflected within the object. The microscope also includes a first acoustooptic scanning device for scanning a plurality of bursts of the electromagnetic energy over a surface of the absorbing layer to generate acoustic waves in the object. A second acoustooptic scanning device is provided for scanning a probe beam at a plurality of positions on the reflecting surface of the opto-acoustic transducer. A housing houses the opto-acoustic transducer and the first and second acoustooptic scanning devices to define an optical needle probe.

Further in carrying out the above objects and other objects of the present invention, a 3-D acoustic microscope adapted to be used in a system for 3-D acoustic microscopy to examine an object internally is provided. The object is capable of converting a burst of electromagnetic energy into a thermal pulse so that the thermal pulse propagates as an acoustic wave in the object and is internally reflected within the object. The microscope includes a first acoustooptic scanning device for scanning a plurality of bursts of the electromagnetic energy over a surface of the object to generate acoustic waves in the object and a second acoustooptic scanning device for scanning a probe beam at a plurality of positions on the surface of the object. The microscope also includes a housing for housing the first and second acoustooptic scanning devices to define an optical needle probe.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

In contrast to the prior art, the method and system of the present invention provides 3-D acoustic microscopy using short optical pulses which are highly focused so that the excitation aperture is comparable to an acoustic wavelength. If confined to an aperture comparable to a wavelength, then the excitation will launch spherical waves into the specimen under study.

Figure 1:
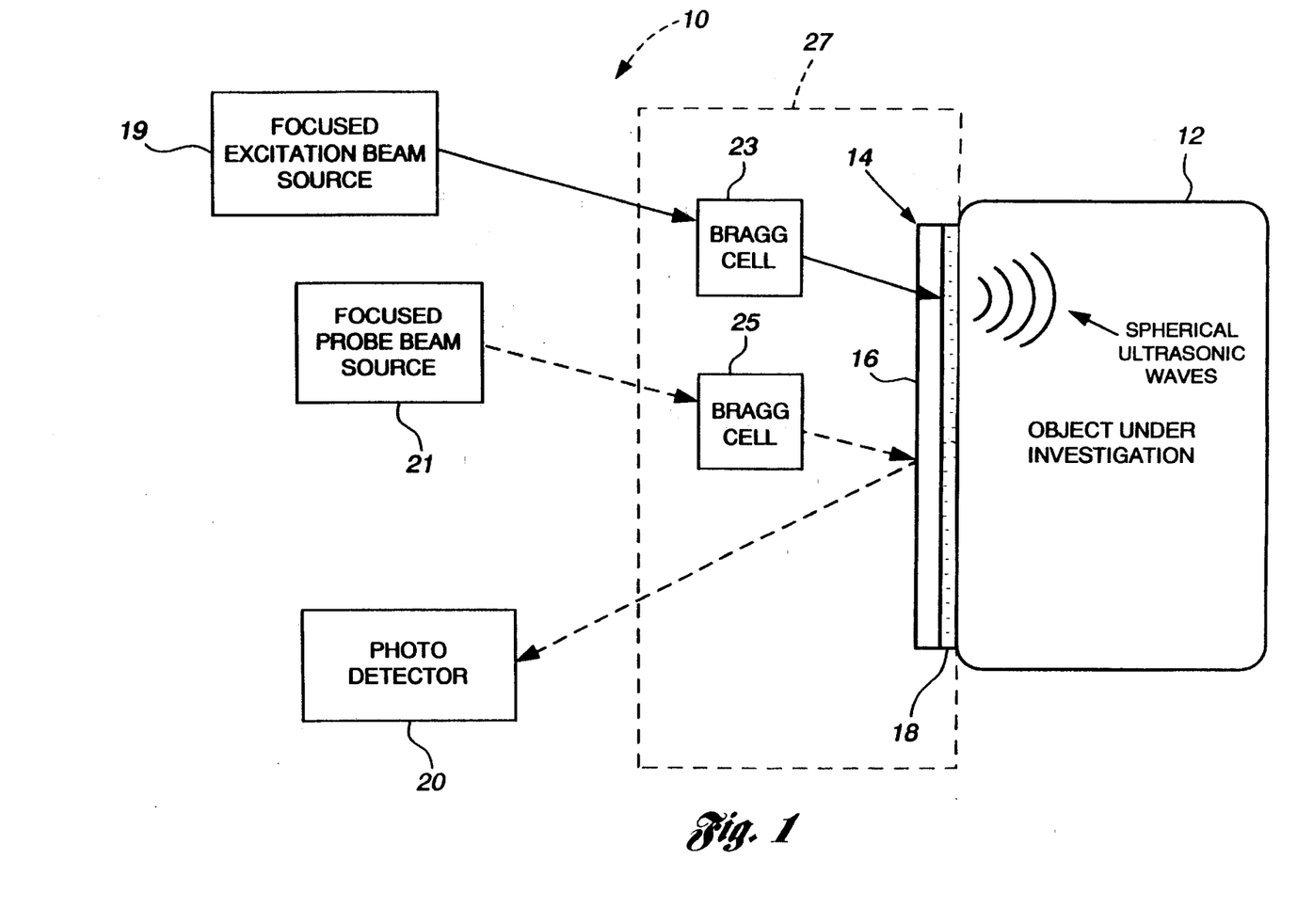
FIG. 1 is a schematic view of a 3-D optically excited acoustic microscope with optical detection.

One possible embodiment of a 3-D microscope system exploiting this principle is generally illustrated at 10 in FIG. 1. A sample or object under investigation 12 is opto-acoustically coupled to a transducer, generally indicated at 14, which includes optically absorbing and reflecting materials. For pathological samples, the object 12 is an internal organ in intimate contact with the transducer 14 insuring coupling of ultrasonic pulses from the transducer 14 to the tissue sample.

The transducer 14 includes a material layer 16 semi-transparent at the optical excitation wavelength and having a thickness preferably equal to one quarter of an ultrasonic wavelength, $\lambda$, at the primary ultrasonic frequency of operation. A thin metal film or absorbing layer 18 (e.g. aluminum) is deposited onto one surface of the semi-transparent layer 16. The thin film 18 is an optical absorber, converting a laser pulse from a source 19 into a thermal pulse which then propagates as a sound wave in the object under investigation 12.

The semi-transparent layer or substrate 16 is typically chosen to be $\lambda/4$ thick so that the absorber-object interface is mechanically clamped at the primary operating frequency, $\lambda$. The absorbing layer 18 may be on either surface of the substrate layer 16, where the absorbing layer 18 also acts as a partial optical reflector if it is placed on the outer surface of the substrate 16.

Each laser excitation pulse is highly focused onto the absorbing layer 18 so that a thermal wave is generated in an area comparable to $(\lambda)^2$, where the duration of the optical pulse is chosen to maximize acoustic generation at the primary ultrasonic frequency of operation, $\lambda$. The resultant ultrasonic pulse propagates as a spherical wave, interacting with the tissue.

Reflected ultrasonic waves propagate back to the free surface at the substrate-air boundary. This boundary acts as the optical reflector in the opto-acoustic transducer. The modulated surface may be probed or scanned by a focused, continuous wave, laser beam generated by a source 21 and operating at a wavelength different than that of the excitation beam. The spot size diameter of the receive beam, controlled by focusing optics, is on the order of $\lambda/2$, where $\lambda$ is the acoustic wavelength. The beam is reflected or scattered at the substrate-air interface, and collected by light gathering optics. The surface displacement may be measured from the reflected beam by optical filtering, such as with a Fabry-Perot etalon and an intensity detector.

The excitation beam generated by the source 19 is preferably scanned over the transducer 14 acousto-optically by a first acoustooptic scanning device such as a Bragg cell 23.

In like fashion, the probe beam generated by the source 21 is scanned over the transducer 14 either mechanically, by motor-controlled mirrors, or acousto-optically by a second acoustooptic scanning device such as a Bragg cell 25.

For each scan position, a generating laser pulse propagates ultrasonic radiation into the object under investigation 12. The scattered or reflected sound is detected by the probe beam and the procedure is repeated for other positions. Obviously, the probe-beam must be scanned over the surface of the transducer 14 independent of excitation beam scanning if a single optical detector such as a photodetector 20 is used for detection.

Figure 2A:
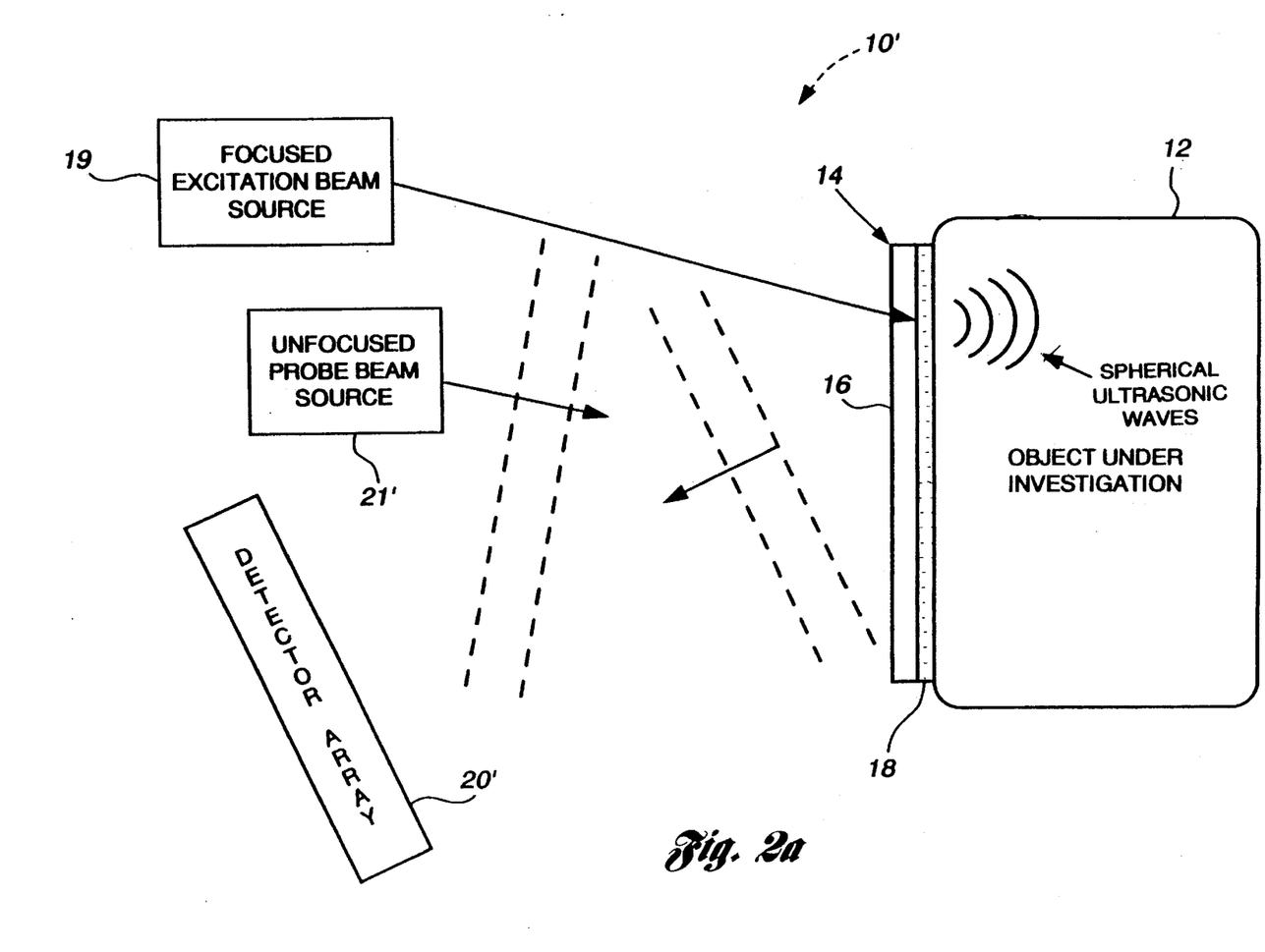
FIG. 2a is a view similar to the view of FIG. 1 wherein optical detection is accomplished with an unfocused probe beam source and an array of coherent optical detectors.

Alternatively, the receive beam can be unfocused as generated by unfocused probe beam source 21' with detection by an array of (coherent) optical detectors 20' as shown in FIG. 2a. The system of FIG. 2a is generally indicated at 10'. Some optical magnification may be needed between the transducer 14 and the detecting array 20' to ensure that each element corresponds to the light reflected from an area of the transducer 14 comparable to the size of the excitation area (i.e., one optical detector element corresponds to an equivalent acoustic element at the surface of the transducer 14). A preferred optical detecting element is disclosed in the above-noted patent application and is also discussed now with reference to FIG. 2b.

Figure 2B:
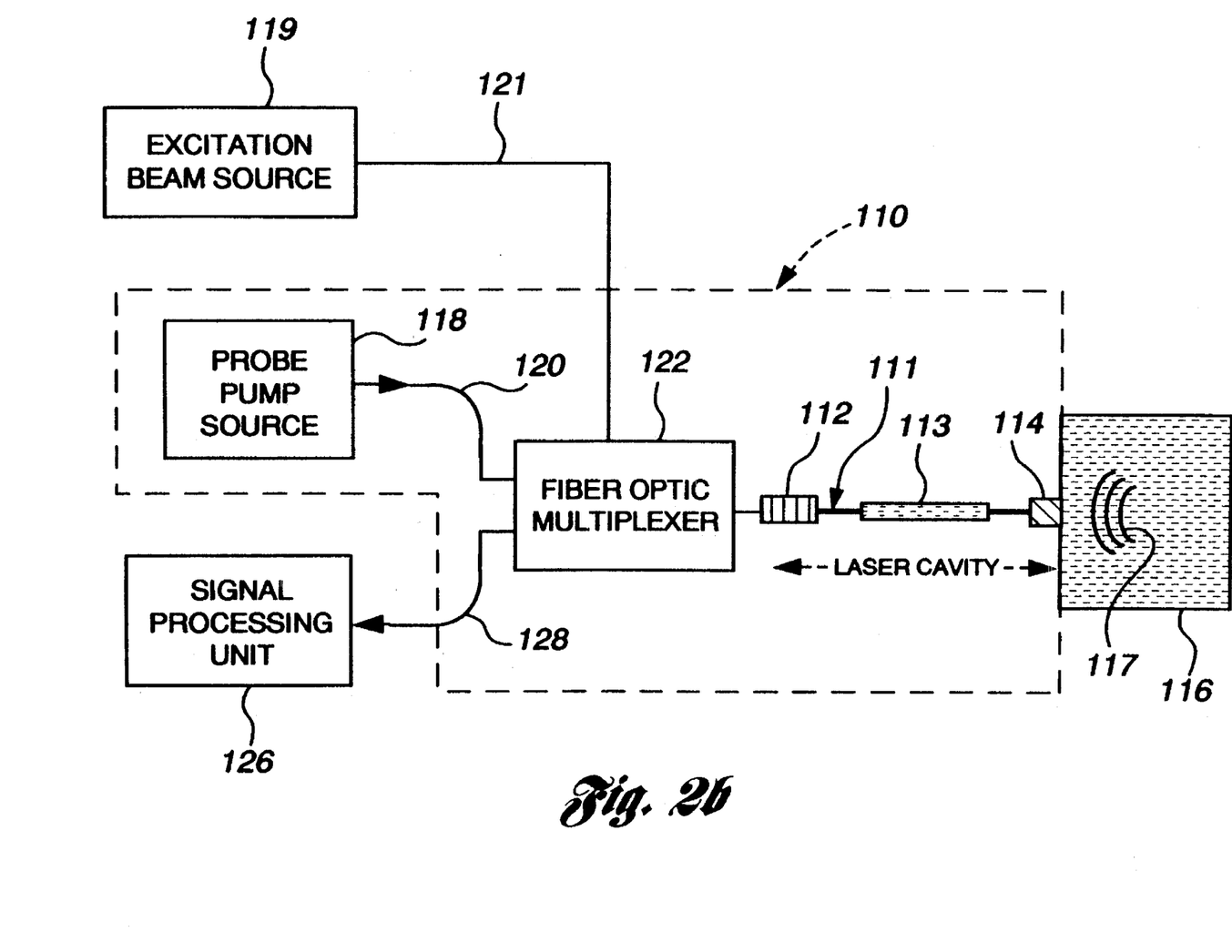
FIG. 2b is a schematic view of an optoacoustic detector with a single optical fiber for use in the method and system of the present invention.

In general, an opto-acoustic detector, generally indicated at 110 in FIG. 2b, is particularly useful in high frequency ultrasound array imaging. The opto-acoustic detector 110 includes a fiber laser for generating optical frequencies related to ultrasound pressure waves incident on the detector. The optical cavity of the fiber laser is modulated by incident acoustic pressure such that changes in optical path length and phase are induced, modulating the optical frequency. The optical cavity is disposed such that its cross-sectional area perpendicular to the optical path is less than or comparable to $\lambda^2$, where $\lambda$ is the wavelength of the incident ultrasound.

The laser cavity has an optical fiber, generally indicated at 111, bounded by first and second reflectors 112 and 114, respectively, on opposite sides of the laser cavity. The reflectors 112 and 114 are disposed such that a single longitudinal mode is supported by the laser cavity.

The detector 110 includes an integrated narrowband reflector 112 which can be placed directly in the optical fiber 111 to limit lasing to a single longitudinal mode in the absence of acoustic modulation.

The second reflector 114 is acoustically coupled to a medium 116 supporting the ultrasound radiation or waves 117.

Either reflector 112 and/or reflector 114 have a frequency response which limits the linewidth of the laser output, thereby enabling single mode operation.

The opto-acoustic detector also includes an active medium 113 which is a section or portion of the optical fiber 111 doped with a gain material that converts incident pump to laser power.

Excitation beam power is delivered through the laser cavity from an external excitation beam source 119 via an optical fiber 121 and coupled to the detector's laser cavity by a fiber-optic multiplexer 122.

Pump power is delivered to the laser cavity from an external probe pump source 118 via an optical fiber 120 and coupled to the detector's laser cavity by the fiber-optic multiplexer 122. The signal power is recovered from the detector 110 through the multiplexer 122, or another output coupling device, and transmitted to a signal processing unit 126 via another optical fiber 128. The unit 126 is responsible for generating an output signal corresponding to the received acoustic pressure incident on the detector 110.

An enhancement to the ultrasound detector 110 is an acoustic signal enhancing feature. This feature allows for greater surface displacements involving the aforementioned broadband reflector 114. The enhanced displacements cause greater fluctuations in the optical path length of the fiber laser cavity, thereby increasing the sensitivity of the detectors 110 as described in detail in the above-noted application.

A further extension of the present invention is the use of the fiber-optic ultrasound detectors 110 in high density, high frequency arrays in direct contact with the specimen under investigation. In arrays of this type, the equivalent ultrasound element size is determined by the sensing area of the optical detector 110. For the fiber-optic device, the sensing area is essentially the cross-sectional area of the fiber core, typically comparable to or less than $\lambda^2$, even at ultrasound operating frequencies greater than 500 MHz. The reduced element size permits closely spaced optical detectors 110, enabling high density arrays for high frequency imaging. In addition, high density fiber arrays can deliver optical excitation pulses to create an acoustic transmitting array. The wavelength of the excitation pulse is selected to be different than the lasing wavelength of the fiber cavity. Either the mirror absorbs the excitation pulse at this wavelength, or the mirror is transparent to this wavelength and passes the excitation pulse to an appropriate absorber.

Referring again to FIG. 2a, the basic recording is repeated as the focused excitation pulse is scanned over precisely the same surface probed or scanned by the unfocused probe beam. This means that if there are N elements in the optical detector array, then there will be $N^2$ recordings over a two-dimensional aperture. In general, the number of firing positions can be arbitrary. Acoustooptic devices, such as the Bragg cells 23 and 25, have been omitted from FIG. 2a for purposes of simplicity.

Figure 3:
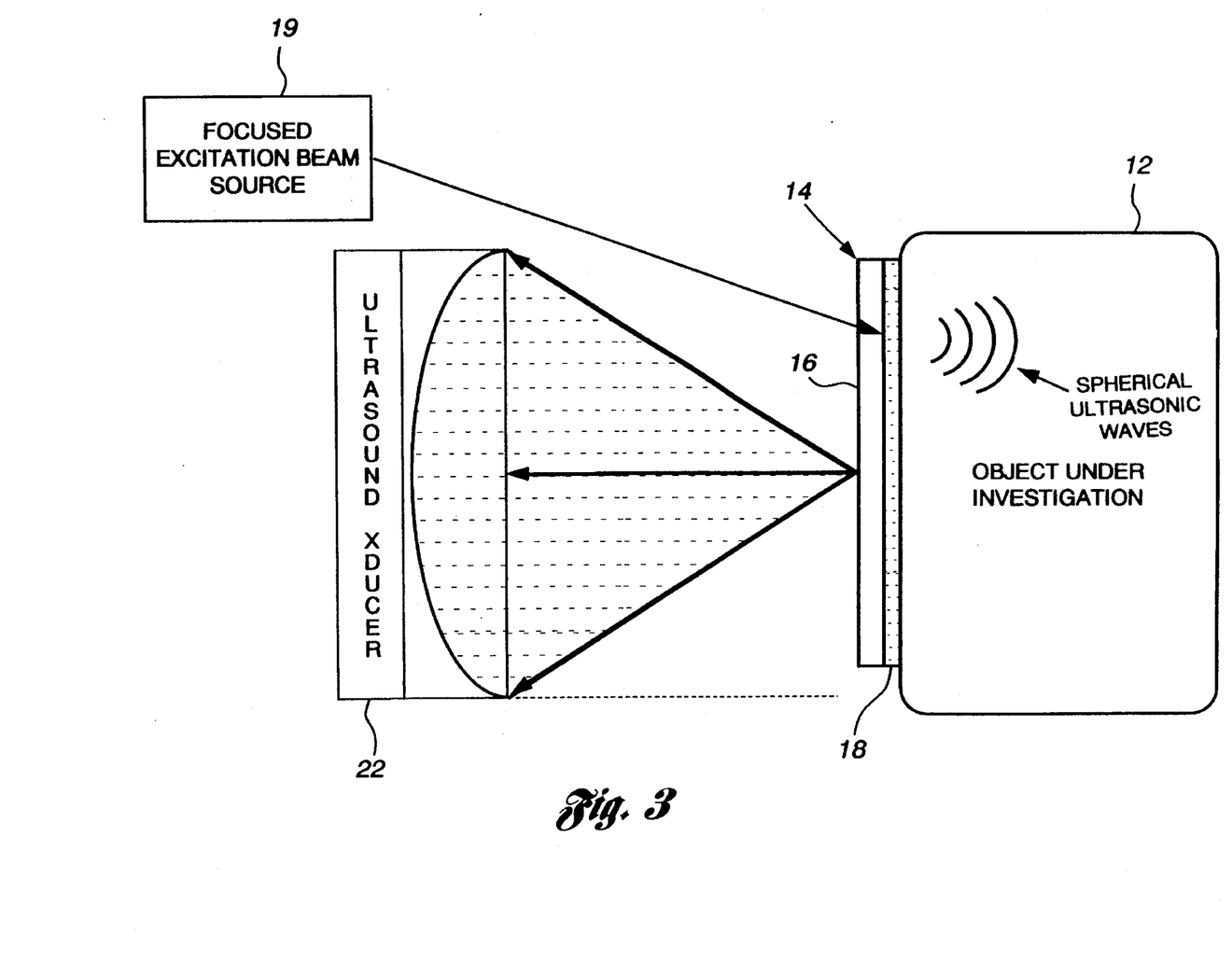
FIG. 3 is a schematic view of a 3-D optically excited acoustic microscope with acoustic detection.

A slight variation of the system of FIG. 2a is illustrated by the system in FIG. 3, which utilizes acoustic detection. Optical detection of acoustic pulses is inherently insensitive. Although it is anticipated that complete optical detection will have sufficient signal to noise ratio to permit high frequency microscopic imaging, for applications needing high sensitivity, direct piezoelectric detection can be used. A highly focused, single element conventional ultrasonic microscope transducer 22 is used in the system of FIG. 3 to detect the reflected ultrasonic wave. The transducer 22 is focused onto the surface of the opto-acoustic transducer 14, where the focal spot is confined to a region comparable to $(\lambda)^2$ (i.e., f/number of about 1 for the ultrasonic lens). The transducer 22 is scanned in a plane parallel to the face of the opto-acoustic transducer 14 recording signals equivalent to the scanned optical probe beam system of FIG. 1.

Figure 4:
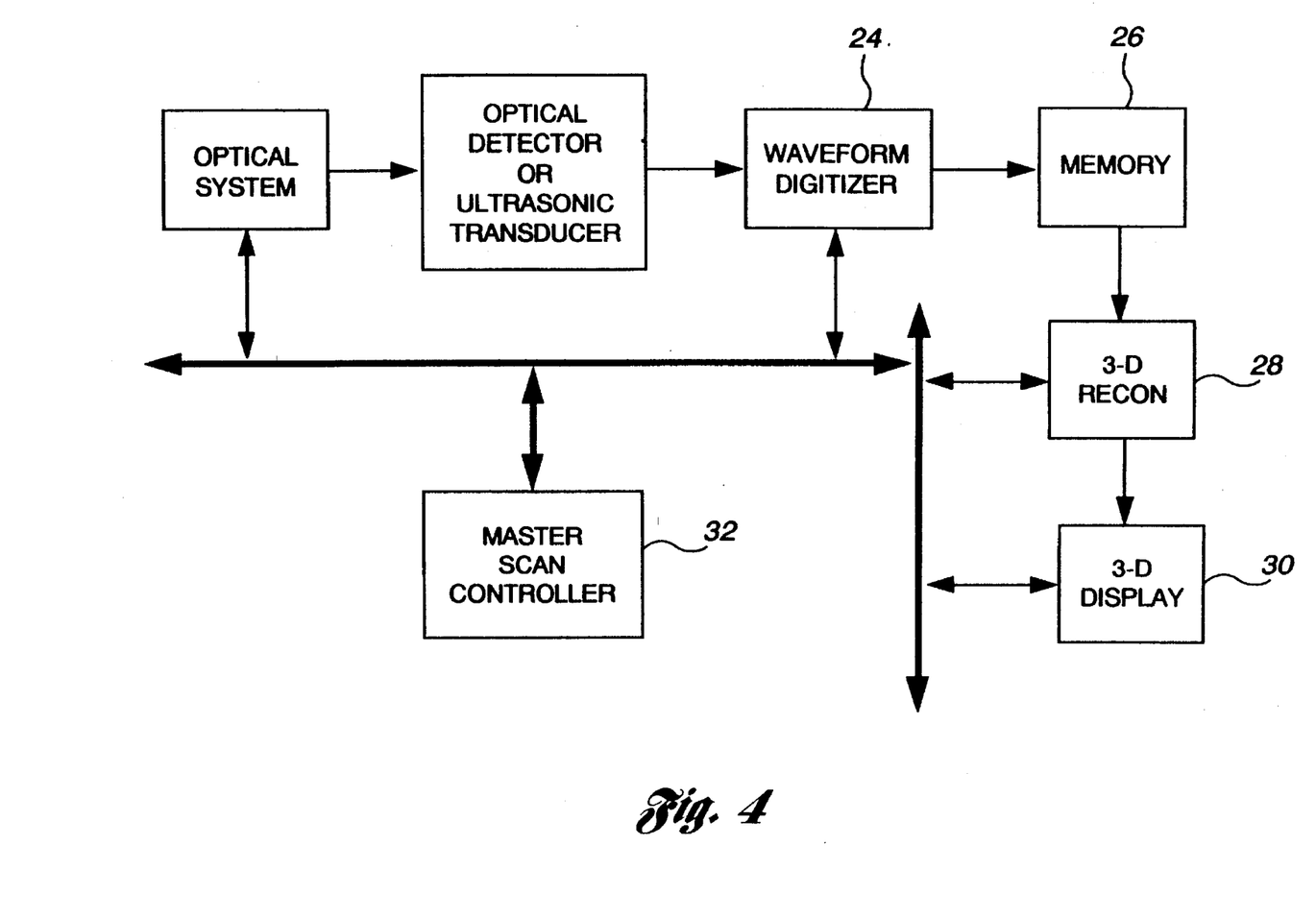
FIG. 4 is a block diagram of a 3-D optically excited acoustic microscope.

A schematic view of the three-dimensional acoustic microscope system using the optical excitation technique described with reference to FIGS. 1, 2a, 2b and 3 is presented in FIG. 4. A radio-frequency waveform (100–1000 MHz, depending on the microscope application) output from either the optical detector 20 or the ultrasonic transducer 22 is digitized using a waveform recorder or digitizer 24. The output of this recorder 24 for each firing is stored in a memory 26 until the entire surface of the opto-acoustic transducer 14 has been scanned. These data are then reconstructed using 3-D synthetic aperture beam forming equations within an appropriately programmed computer as indicated at block 28 to permit complete spherical focus on both transmit and receive. Such reconstruction routines are currently used in low-frequency ultrasonic imaging with 1-D arrays. These standard methods can be easily extended for 2-D arrays, resulting in full 3-D reconstructions.

The output of the reconstruction hardware is then displayed using a conventional 3-D display system 30 currently employed in medical imaging. The entire data acquisition, reconstruction and display system should be synchronized by a master scan controller 32.

The systems shown in FIGS. 1–3 are conceptually simple. Nevertheless, they produce truly three-dimensional images, with high resolution maintained over a large depth of field.

Such systems can have a dramatic impact on the current practice of clinical pathology, especially if they can both provide detailed information equivalent to the highest performance optical microscopes currently in routine use and be incorporated into the tip of a conventional biopsy needle for in situ, real-time imaging. The first and second acoustooptic devices, Bragg cells 23 and 25, together with the opto-acoustic transducer 14 define a 3-D acoustic microscope when placed in a housing, indicated in phantom at 27 in FIG. 1. The lines leading from the sources 19 and 21 and to the photodetector 20 may comprise a single optical fiber and may have the same general configuration as shown in FIG. 2b, wherein a single optical fiber 111 serves multiple purposes.

In addition to medical applications, there may be several uses of this technology in non-destructive evaluation (NDE) of materials. In such uses, there may not be a need for an opto-acoustic transducer. The disclosed microscopes can replace mechanically scanned systems in all NDE applications. Moreover, in applications permitting needle insertion, such as NDE of soft plastics, the electronic scanning capability of this system is vastly superior to traditional mechanical scanning.

While the best mode for carrying out the invention has been described in detail, those familiar with the art to which this invention relates will recognize various alternative designs and embodiments for practicing the invention as defined by the following claims.

What is claimed is:

1. A method for examining an object internally, the method comprising the steps of:

positioning an opto-acoustic transducer having a reflecting surface and an absorbing layer capable of converting a burst of electromagnetic energy into a thermal pulse relative to the object so that the thermal pulse propagates as an acoustic wave in the object and is internally reflected within the object;

scanning a plurality of bursts of the electromagnetic energy over a surface of the absorbing layer to obtain acoustic waves in the object;

detecting acoustic waves reflected within the object at a plurality of positions on the reflecting surface of the opto-acoustic transducer to generate resultant signals;

calculating a 3-D representation of the object from the resultant signals; and displaying the 3-D representation as an image.

2. The method as claimed in claim 1 wherein the bursts of electromagnetic energy are pulses of laser light.

3. The method as claimed in claim 2 wherein the acoustic waves have a primary wavelength, $\lambda$, and wherein the method further comprises the step of focusing the pulses of laser light so that each thermal pulse is generated at an area of the absorbing layer approximately equal to $\lambda^2$ so that the acoustic sound waves are spherical waves.

4. The method as claimed in claim 1 wherein the bursts of electromagnetic energy are pulses of laser light and wherein the absorbing layer is a material layer of the opto-acoustic transducer.

5. The method as claimed in claim 4 wherein the absorbing layer of the opto-acoustic transducer is a thin metallic film.

6. The method as claimed in claim 5 wherein the opto-acoustic transducer includes an optically semi-transparent substrate layer having a thickness of approximately $\lambda/4$ and wherein the metallic film is formed as a surface layer on the substrate layer.

7. The method as claimed in claim 1 wherein the step of detecting includes the step of scanning the reflecting surface of the opto-acoustic transducer with a focused, continuous-wave laser beam operating at a wavelength different than the wavelength of the bursts of electromagnetic energy.

8. The method as claimed in claim 7 wherein the reflecting surface is a surface of the absorbing layer of the opto-acoustic transducer.

9. The method as claimed in claim 1 wherein the acoustic waves have a primary wavelength, $\lambda$, and wherein the step of detecting includes the step of scanning a probe beam having spot size with a diameter less than $\lambda$, over the reflecting surface of the opto-acoustic transducer at a plurality of scan positions.

10. The method as claimed in claim 1 wherein the step of detecting is accomplished with an array of opto-acoustic detectors.

11. The method as claimed in claim 1 wherein the acoustic waves have a primary wavelength, $\lambda$, and wherein the step of detecting is accomplished with an ultrasonic microscope transducer for focusing an acoustic spot on the surface of the object, the spot having an area approximately equal to $\lambda^2$ and wherein the microscope transducer is utilized to scan in a plane substantially parallel to the surface of the object.

12. The method as claimed in claim 1 wherein the step of calculating is based on 3-D synthetic aperture beam-forming equations.

13. A method for examining an object internally, the object being capable of converting a burst of electromagnetic energy into a thermal pulse which propagates as an acoustic wave in the object and is internally reflected within the object, the method comprising the steps of:

scanning a plurality of bursts of the electromagnetic energy over a surface of the object to generate acoustic waves in the object;

detecting the acoustic waves reflected within the object at a plurality of positions on the surface of the object to generate resultant signals;

calculating a 3-D representation of the object from the resultant signals; and displaying the 3-D representation as an image.

14. The method as claimed in claim 13 wherein the bursts of electromagnetic energy are pulses of laser light.

15. The method as claimed in claim 14 wherein the acoustic waves have a primary wavelength, $\lambda$, and wherein the method further comprises the step of focusing the pulses of laser light so that each thermal pulse is generated at an area of the object approximately equal to $\lambda^2$ so that the acoustic sound waves are spherical waves.

16. The method as claimed in claim 13 wherein the step of detecting includes the step of scanning the surface of the object with a focused, continuous-wave laser beam operating at a wavelength different than the wavelength of the bursts of electromagnetic energy.

17. The method as claimed in claim 13 wherein the acoustic waves have a primary wavelength, $\lambda$, and wherein the step of detecting includes the step of scanning a probe beam having spot size with a diameter less than $\lambda$, over the surface of the object at a plurality of scan positions.

18. The method as claimed in claim 17 wherein the step of detecting is accomplished with an array of opto-acoustic detectors.

19. The method as claimed in claim 17 wherein the acoustic waves have a primary wavelength, $\lambda$, and wherein the step of detecting is accomplished with an ultrasonic microscope transducer for focusing an acoustic spot on the surface of the object, the spot having an area approximately equal to $\lambda^2$ and wherein the transducer is utilized to scan in a plane substantially parallel to the surface of the object.

20. The method as claimed in claim 17 wherein the step of calculating is based on 3-D synthetic aperture beamforming equations.

21. A system for examining an object internally, the system comprising:

an opto-acoustic transducer adapted to be acoustically coupled to the object and having a reflecting surface and an absorbing layer capable of converting a burst of electromagnetic energy into a thermal pulse so that the thermal pulse propagates as an acoustic wave in the object and is internally reflected within the object;

an excitation beam scanner for scanning a plurality of bursts of the electromagnetic energy over a surface of the absorbing layer to obtain acoustic waves in the object;

a detector for detecting the acoustic waves reflected within the object at a plurality of positions on the reflecting surface of the opto-acoustic transducer to generate resultant signals;

a calculator for calculating a 3-D representation of the object from the resultant signals; and a display for displaying the 3-D representation as an image.

22. The system as claimed in claim 21 wherein the bursts of electromagnetic energy are pulses of laser light.

23. The system as claimed in claim 22 wherein the acoustic waves have a primary wavelength, $\lambda$, and wherein the system further comprises an optical component for focusing the pulses of laser light so that each thermal pulse is generated at an area of the absorbing layer approximately equal to $\lambda^2$ so that the acoustic sound waves are spherical waves.

24. The system as claimed in claim 23 wherein the absorbing layer of the opto-acoustic transducer is a thin metallic film.

25. The system as claimed in claim 24 wherein the opto-acoustic transducer includes an optically semi-transparent substrate layer having a thickness of approximately $\lambda/4$ and wherein the metallic film is formed as a surface layer on the substrate layer.

26. The system as claimed in claim 21 wherein the bursts of electromagnetic energy are pulses of laser light and wherein the absorbing layer is a material layer of the opto-acoustic transducer.

27. The system as claimed in claim 26 further comprising an optical fiber and wherein the probe beam is delivered to the probe beam scanner by the optical fiber.

28. The system as claimed in claim 21 wherein the detector includes a probe beam scanner for scanning the reflecting surface of the opto-acoustic transducer with a focused, continuous-wave laser beam operating at a wavelength different than a wavelength of the bursts of electromagnetic energy.

29. The system as claimed in claim 28 wherein the reflecting surface is a surface of the absorbing layer of the opto-acoustic transducer.

30. The system as claimed in claim 21 wherein the acoustic waves have a primary wavelength, $\lambda$, and wherein the detector includes a probe beam scanner for scanning a probe beam having spot size with a diameter less than $\lambda$, over the reflecting surface of the opto-acoustic transducer at a plurality of scan positions.

31. The system as claimed in claim 30 wherein at least one of the scanners includes an electronically driven acoustooptic device.

32. The system as claimed in claim 31 wherein the acoustooptic device is a Bragg cell.

33. The system as claimed in claim 30 wherein the opto-acoustic transducer including the absorbing layer and the reflecting surface, the probe beam scanner and the excitation beam scanner are housed in a housing to define an optical needle probe.

34. The system as claimed in claim 30 further comprising a single optical fiber and wherein the probe beam is delivered to the probe beam scanner, the excitation beam is delivered to the excitation beam scanner and a detecting beam is delivered to the detector by the single optical fiber.

35. The system as claimed in claim 21 further comprising an optical fiber and wherein the excitation beam is delivered to the excitation beam scanner by the optical fiber.

36. The system as claimed in claim 34 wherein the detector includes a photodetector array and wherein a detecting beam is returned to the photodetector array by the optical fiber.

37. The system as claimed in claim 21 wherein the detector includes an array of opto-acoustic detectors.

38. The system as claimed in claim 21 wherein the acoustic waves have a primary wavelength, $\lambda$, and wherein the detector includes an ultrasonic microscope transducer for focusing an acoustic spot on the surface of the object, the spot having an area approximately equal to $\lambda^2$ and wherein the microscope transducer is utilized to scan in a plane substantially parallel to the surface of the object.

39. The system as claimed in claim 21 wherein the calculator includes a programmed computer for computing the 3-D representation based on 3-D synthetic aperture beam-forming equations.

40. A system for examining an object internally, the object being capable of converting a burst of electromagnetic energy into a thermal pulse which propagates as an acoustic wave in the object and is internally reflected within the object, the system comprising:

an excitation beam scanner for scanning a plurality of bursts of the electromagnetic energy over a surface of the object to generate acoustic waves in the object;

a detector for detecting acoustic waves reflected within the object at a plurality of positions on the surface of the object to generate resultant signals;

a calculator for calculating a 3-D representation of the object from the resultant signals; and a display for displaying the 3-D representation as an image.

41. The system as claimed in claim 40 wherein the bursts of electromagnetic energy are pulses of laser light.

42. The system as claimed in claim 41 wherein the acoustic waves have a primary wavelength, $\lambda$, and wherein the system further comprises an optical element for focusing the pulses of laser light so that each thermal pulse is generated at an area of the object approximately equal to $\lambda^2$ so that the acoustic sound waves are spherical waves.

43. The system as claimed in claim 40 wherein the detector includes a probe beam scanner for scanning the surface with a focused, continuous-wave laser beam operating at a wavelength different than the wavelength of the bursts of electromagnetic energy.

44. The system as claimed in claim 40 wherein the acoustic waves have a primary wavelength, $\lambda$, and wherein the detector includes a probe beam scanner for scanning a probe beam having spot size with a diameter less than $\lambda$, over the surface of the object at a plurality of scan positions.

45. The system as claimed in claim 44 wherein at least one of the scanners includes an electronically driven acoustooptic device.

46. The system as claimed in claim 45 wherein the acoustooptic device is a Bragg cell.

47. The system as claimed in claim 44 further comprising a housing wherein the probe beam scanner and the excitation beam scanner are housed in the housing to define an optical needle probe.

48. The system as claimed in claim 44 further comprising an optical fiber and wherein the probe beam is delivered to the probe beam scanner by the optical fiber.

49. The system as claimed in claim 44 further comprising an optical fiber and wherein the excitation beam is delivered to the excitation beam scanner by the optical fiber.

50. The system as claimed in claim 49 wherein the detector includes a photodetector array and wherein a detecting beam is returned to the photodetector array by the optical fiber.

51. The system as claimed in claim 44 further comprising a single optical fiber and wherein the probe beam is delivered to the probe beam scanner, the excitation beam is delivered to the excitation beam scanner and a detecting beam is delivered to the detector by the single optical fiber.

52. The system as claimed in claim 40 wherein the detector includes an array of opto-acoustic detectors.

53. The system as claimed in claim 40 wherein the acoustic waves have a primary wavelength, $\lambda$, and wherein the detector includes an ultrasonic microscope transducer for focusing an acoustic spot on the surface of the object, the spot having an area approximately equal to $\lambda^2$ and wherein the transducer is utilized to scan in a plane substantially parallel to the surface of the object.

54. The system as claimed in claim 40 wherein the calculator includes a programmed computer for calculating the 3-D representation based on 3-D synthetic aperture beam-forming equations.

55. A 3-D acoustic microscope adapted to be used in a system for 3-D acoustic microscopy to examine an object internally, the microscope comprising:

an opto-acoustic transducer adapted to be coupled to the object and including an optically reflecting surface and an absorbing layer capable of converting a burst of electromagnetic energy into a thermal pulse so that the thermal pulse propagates as an acoustic wave in the object and is internally reflected within the object;

a first acoustooptic scanning device for scanning a plurality of bursts of the electromagnetic energy over a surface of the absorbing layer to generate acoustic waves in the object;

a second acoustooptic scanning device for scanning a probe beam at a plurality of positions on the reflecting surface of the opto-acoustic transducer; and a housing for housing the opto-acoustic transducer and the first and second acoustooptic scanning devices to define an optical needle probe.

56. The microscope as claimed in claim 55 wherein at least one of the scanning devices is an electronically driven acoustooptic Bragg cell.

57. A 3-D acoustic microscope adapted to be used in a system for 3-D acoustic microscopy to examine an object internally, the object being capable of converting a burst of electromagnetic energy into a thermal pulse so that the thermal pulse propagates as an acoustic wave in the object and is internally reflected within the object, the microscope comprising:

a first acoustooptic scanning device for scanning a plurality of bursts of the electromagnetic energy over a surface of the object to generate acoustic waves in the object;

a second acoustooptic scanning device for scanning a probe beam at a plurality of positions on the surface of the object; and a housing for housing the first and second acoustooptic scanning devices to define an optical needle probe.

58. The microscope as claimed in claim 57 wherein at least one of the scanning devices is an electronically driven acoustooptic Bragg cell.

* * * * *